(12) United States Patent
Kratzer et al.

(10) Patent No.: US 8,486,337 B2
(45) Date of Patent: Jul. 16, 2013

(54) DEVICE FOR ANALYZING THE COAGULATION OR AGGREGATION BEHAVIOR OF BLOOD

(75) Inventors: Michael Kratzer, Munich (DE); Volker Freiherr Von Der Goltz, Seeon (DE)

(73) Assignee: VDG-Von der Goltz GmbH, Seeon (DE)

( * ) Notice: Subject to any disclaimer, the term of this patent is extended or adjusted under 35 U.S.C. 154(b) by 710 days.

(21) Appl. No.: 11/587,176

(22) PCT Filed: Apr. 14, 2005

(86) PCT No.: PCT/DE2005/000678
§ 371 (c)(1),
(2), (4) Date: Mar. 6, 2007

(87) PCT Pub. No.: WO2005/103688
PCT Pub. Date: Nov. 3, 2005

(65) Prior Publication Data
US 2007/0212744 A1  Sep. 13, 2007

(30) Foreign Application Priority Data
Apr. 21, 2004  (DE) .......................... 10 2004 019 374

(51) Int. Cl.
*G01N 33/86* (2006.01)
(52) U.S. Cl.
USPC ............................................. 422/73; 436/69
(58) Field of Classification Search
None
See application file for complete search history.

(56) References Cited

U.S. PATENT DOCUMENTS

| | | | |
|---|---|---|---|
| 5,051,239 A | * | 9/1991 | von der Goltz ................. 422/73 |
| 5,602,037 A | * | 2/1997 | Ostgaard et al. ................ 436/69 |
| 5,854,076 A | | 12/1998 | Kundu et al. |

FOREIGN PATENT DOCUMENTS

| | | |
|---|---|---|
| DE | 32 47 815 A1 | 12/1982 |
| EP | 0 635 720 A2 | 7/1994 |
| EP | 0 716 744 B1 | 6/1995 |
| WO | WO 97/34698 A1 | 9/1997 |
| WO | WO 97/41431 A1 | 11/1997 |
| WO | WO 01/55714 A2 | 8/2001 |

OTHER PUBLICATIONS

In Vitro Bleeding Test—A Sensitive Method for the Detection of Platelet Function Impairment and a Potential Test for the Control of Low-Dose Aspirin Efficacy, V. Krestschmer et al., Blut Springer-Verlag, 1989 59:188, pp. 593-602.

* cited by examiner

*Primary Examiner* — Sally Merkling
(74) *Attorney, Agent, or Firm* — Karl F. Milde, Jr.; Eckert Seamans Cherin & Mellott, LLC

(57) ABSTRACT

A device is provided for analyzing the coagulation and/or behavior of blood. The blood flows through an opening (9) that is disposed in a porous part (5) while a substance which influences blood aggregation can be delivered to the blood. A preliminary diffuser chamber (3) from which blood flows to the opening (9) is mounted upstream of the opening (9), and/or a secondary diffuser chamber (4) into which blood flows from the opening (9) is mounted downstream of the opening (9). The substance is arranged on the wall of the preliminary diffuser chamber (3) and/or the secondary diffuser chamber (4) in the form of a coating (8).

27 Claims, 3 Drawing Sheets

DEVICE FOR ANALYZING THE COAGULATION OR AGGREGATION BEHAVIOR OF BLOOD

BACKGROUND OF THE INVENTION

The current invention pertains to a device for the analysis of coagulation and/or aggregation reaction of blood.

Such devices are already known. For example DE 32 47 815 A1 describes a device for the measurement of the bleeding time in vitro, where the blood is fed under constant pressure gradient through an opening, whereas it is provided with a device for the direct or indirect measurement of the resulting blood stream. One side of the opening is made of a porous material, which is preferably a filtering material, which shows a pore size in a range between 0.01 and 5 μm. This piece is mounted in a case in such a way that the blood extracted from a supply container and fed over a capillary of the opening is mainly flowing through the opening and no blood is running past the side of the piece.

From this prior art it is also known that the material of the piece contained in this opening is saturated with a solution which will aggregate or coagulate the blood platelets of the blood, before starting the analysis, preferably in adenosine diphosphate (ADP). Also known from this prior art is that the material of the piece contained in the opening is coated with collagen.

By soaking the porous piece with adenosine phosphate or with other substances, the bleeding rates can be imitated with even more precise in vivo conditions, because during a real injury, the injured vessel wall releases adenosine phosphate, thereby inducing the platelets aggregation.

By coating the filtering fibres of the porous piece with collagen, we obtain a better repeatability and a shorter bleeding time, because the filtering fibres coated with collagen from the porous piece in the border area of the opening favor the adhesion of the blood platelets.

It is also known since 1965 how to produce single use pieces for measuring the bleeding time in vitro (Thrombostat 4000, producer: VDG of Goltz GmbH, 83370 Seeon). These single use pieces consisted of a porous material with an opening with a diameter of 150-120 μm and were coated with collagen fibres dispersed in solution and then dried, in order to extend the durability. This is described in detail in U.S. Pat. No. 5,854,076 (column 2, paragraph 1). The single use parts were stored in bags with a drying material, until they were used for measurements in patients. In order to perform the measurement, the dried collagen was supposed to be reconstituted by adding a liquid, so that the collagen fibres were transferred again in the initial hydrated state. In addition, platelets aggregating substances, like for example ADP or $CaCl_2$, could be added, as described in the article "In vitro bleeding test—a simple method for the detection of aspirin effects on platelet function", by Kretschner V, Schikor B., Sohngen D Dietrich G., Thromb. Res., 1989 Dec. 1; 56 (5), pages 593-602.

From EP D 716 744 B1 we also know of a porous separating element which shows an opening that has at least one substance built-in and dried, which at the time of measurement, when blood is streaming through the opening, can be reconstituted, in order to initiate the blood coagulation process or the thrombocyte aggregation in the blood. The substances used to initiate the blood coagulation are either ADP, ristocetine, arachidonic acid, thrombin, epinephrine, thrombocyte activation factor (PAF) or thrombin-receptor-agonist-peptide (TBAP). Furthermore, the porous separating element can contain collagen, which also induces the aggregation of the blood platelets.

A problem of the known addition of adenosine phosphate (ADP) together with collagen consists in the fact that ADP is degraded through polluted ADPases to adenosine, which inhibits the formation of platelets. This is the reason why the ADP concentration must be relatively high, in order to achieve the desired reaction.

SUMMARY OF THE INVENTION

The objective of this invention is to create a device for the analysis of the coagulation and/or aggregation reaction of blood, where measurements can be performed even with a low concentration of substance added to blood, especially a much lower concentration of ADP.

This objective, as well as other objectives which will become apparent from the discussion that follows, are achieved, in accordance with the present invention, by providing a device of the type described above which has a prediffusing chamber disposed upstream of the opening and/or an after-diffusing chamber disposed downstream. The substance which is fed into the blood to influence the blood aggregation is applied in the form of a coating applied to the walls of either the prediffusing chamber or after-diffusing chamber, or both.

The major advantage of the current invention lies in the fact that the known procedure allows for comparable measurements with a much lower ADP concentration. While the above-mentioned known measuring procedure requires an ADP concentration of about $10^{-3}$ M in the area of the porous piece, the device according to this invention can be used with a much lower ADP concentration. This is very advantageous especially for various problems in medicine, for example with the adjustment of certain medication, like chlopidogrel, which reacts over an ADP receptor. In other words, within the current invention, measurements can be performed at equal stability, with a much lower concentration of substance fed into the blood, for example a much lower ADP concentration.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
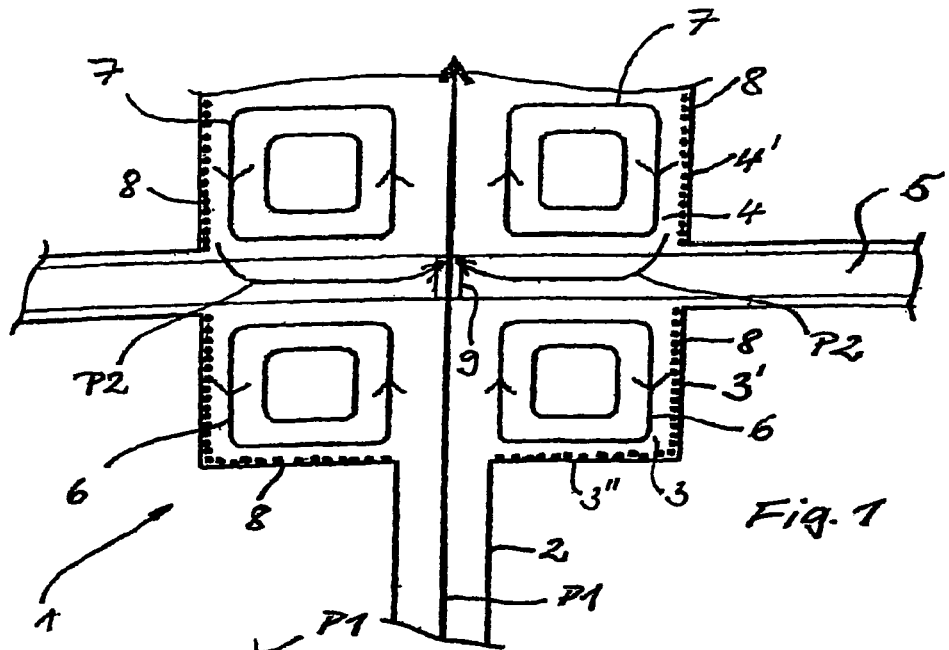
FIG. 1 shows an embodiment that illustrates the principle of the present invention.

The preferred embodiments of the present invention will now be described with reference to FIGS. 1-5 of the drawings. Identical elements in the various figures are designated with the same reference numerals.

The following considerations led to the invention. According to Bernoulli's theorem ($p+½\rho v^2$=const.) the pressure [p] rises in a stream strand which expands (diffusor streaming), because the streaming speed (v) must decrease according to the Law of Continuity. If the diffusor expands suddenly, this sudden pressure increase leads to the stream separation and formation of a so-called eddy water with secondary streaming. The liquid layers close to the walls with low kinetic energy cannot overcome the pressure increase and flow back against the main current direction. We can use this back-streaming close to the walls, to transport certain water-soluble substances, which are applied on the wall, back to desired locations. This principle is employed for the first time in carrying out the present invention.

In connection with the present invention, the concept was conceived, for the first time, to use the above described principle to add a substance, for example ADP, evenly and with an as low concentration as possible, to the streaming blood coming through an opening with a porous piece, during the entire process of measurement. In doing so, the targeted objective was to refrain from the prior known feeding of the substance already contained in the porous piece. The substance is first supplied from a diffusor chamber perfused by blood, which lies before and/or after the opening. The substance is eliminated on the walls of a prediffusing chamber and/or after-diffusing chamber lying before the opening and/or after the opening in a watering device. The substance is slowly fed to the perfused blood through the secondary streaming in the prediffusing chamber and/or the after-diffusing chamber and, in the case of the after-diffusing chamber, is inserted in the material of the porous contrast thereto, the substance is quick flushed out and used, at the prior known feed, from the material or the area of the porous piece.

A disadvantage with the known, simultaneous application of ADP and collagen on the filtering material contained in the opening consists in the fact that the enzymes which degrade the ADP contained in collagen destroy the ADP; that is why the concentration of ADP must be very high. However, for certain problems and measurements, precisely low ADP concentrations are indispensable.

FIG. 1 shows an embodiment suitable for explaining the principle according to the invention. The area of the device for the measurement of the coagulation and/or aggregation of the blood is represented in a diagram and contains a porous piece 5 with an opening 9. There, the porous piece 5 consists of a porous material, for example of a filtering material. The blood extracted from the blood container, not illustrated here, streams in direction of the arrow P1 through a tube 2, for example a capillary, in a prediffusing chamber 3 located before the opening 9, in an after-diffusing chamber 4 beyond the opening 9 and from here into a blood collecting container not illustrated in FIG. 1. Through a compact disposition of the prediffusing and after-diffusing chambers 3, 4 and the porous piece 5 in a casing, not illustrated here, it is ensured that the blood cannot flow sideways past the porous piece 5 and opening 9.

In the prediffusing chamber 3, a substance to be transferred into the blood is applied to the inner walls, either on the entire surface or on areas, or partially, for example in a punctiform coating 8.

Accordingly, this substance to be transferred into the blood can be additionally or exclusively applied in a similar coating 8 on the inner walls of the after-diffusing chamber 4. During the streaming of the prediffusing chamber 3 with blood (direction P1), the blood comes in contact with the coating 8, whereby the substance dissolves and reaches the blood. As during the streaming of the prediffusing chamber 3, the diffusor streaming 6 is formed as illustrated in FIG. 1, the substance dissolved from the coating 8 in this diffusor streaming 6 from the area of the inner walls of the pre-diffusing chamber 3 is transported in direction of the streaming blood towards the opening 9, so that it streams together with the blood through the opening 9.

It is visible, the substance of the coating 8 of the prediffusing chamber 3 is fed into the streaming blood towards the opening 9 relatively quickly and in high concentration, as it is mixed into the streaming blood relatively quickly through the diffusor streaming 6 in the direction of the opening 9, from the side walls 3' and/or the porous piece 5 opposite floor wall 3" in direction of the stream.

In configuration of a coating 8 on the inner surface of the side wall 4' of the after-diffusing chamber 4, the substance which dissolves the coating 8 is mixed into the streaming blood through the diffusor stream 7 from the opening 9 into the after-diffusing chamber 4, inducing a stream P2 in the porous piece 5 which transports the substance directly to the location of the opening 9 or, respectively, to the thrombus which is formed there.

If the coatings 8 are provided both in the prediffusing chamber 3 and after-diffusing chamber 4, the substances are fed to the area of the opening 9 from the walls 3' and/or 3" of the prediffusing chamber 3 and the side wall 4' of the after-diffusing chamber 4. At the same time, the provided coatings 8 in chambers 3, 4 can be different and in different directions.

The term "substance", as used herein, is to be understood as a substance or substances which can be added to blood. At the same time it is possible to think of substances which can enhance or inhibit the aggregation of the blood cells.

The substances are preferably applied in liquid form on the walls of the pre- and/or after-diffusing chamber 3, 4 and dry afterwards. The substance is liquified again, i.e. reconstituted, by adding a liquid medium, for example a saline solution, only while performing a measurement with the present device. This can also occur through the blood itself.

Figure 2:
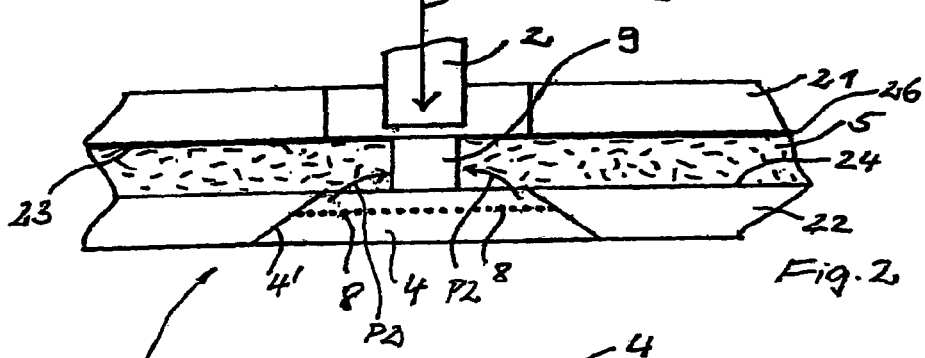
FIGS. 2 and 3 show a schematic embodiment of an especially advantageous form of the device according to the invention.
Figure 3:
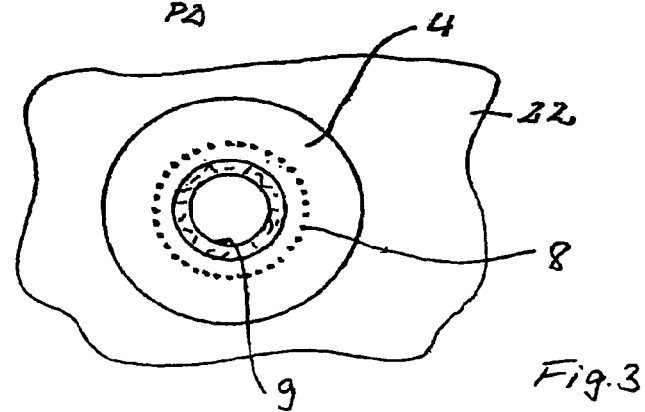

FIGS. 2 and 3 show a particularly preferred embodiment of the invented device. Details of this figures, which have already been explained in relation to FIG. 1, are indicated accordingly. The blood streams in direction of the arrow P1 towards the opening 9, which is contained in a porous piece 5. In the direction of the arrow P1, as seen from behind the opening 9, the blood is streaming into an after-diffusing chamber 4, which is provided with a coat 8 of substance. The after-diffusing chamber 4 preferably shows a coating 8 on the side towards the blood, in form of a ring-shaped coating. Thereby the ring-shaped coating 8 can occur as a continuous line or surface or an interrupted line or surface, especially in form of a line or surface consisting of cvonsecutively ranked coating points. The side wall 4' of the after-diffusing chamber 4 will preferably narrow transversal from the outside, in direction of the opening 9. The bevel will have the form of a cone. FIG. 3 shows a picture of the opening as seen from the after-diffusing chamber 4.

The pieces 21 and 22 show beds 23, 24 for the porous piece 5, in order to make sure that the blood, when streaming through the opening 9, does not flow sideways besides the porous piece 5 and the opening 9, but directly from the capillary tube 2, through the opening 9 into the after-diffusing chamber 4, and from there streams into a blood collecting container (not described in detail herein).

On the side of the porous piece 5 towards the blood stream, a collagen layer 26 can be applied according to FIG. 2, at least in the area surrounding the opening 9, as has been mentioned above.

Figure 4:
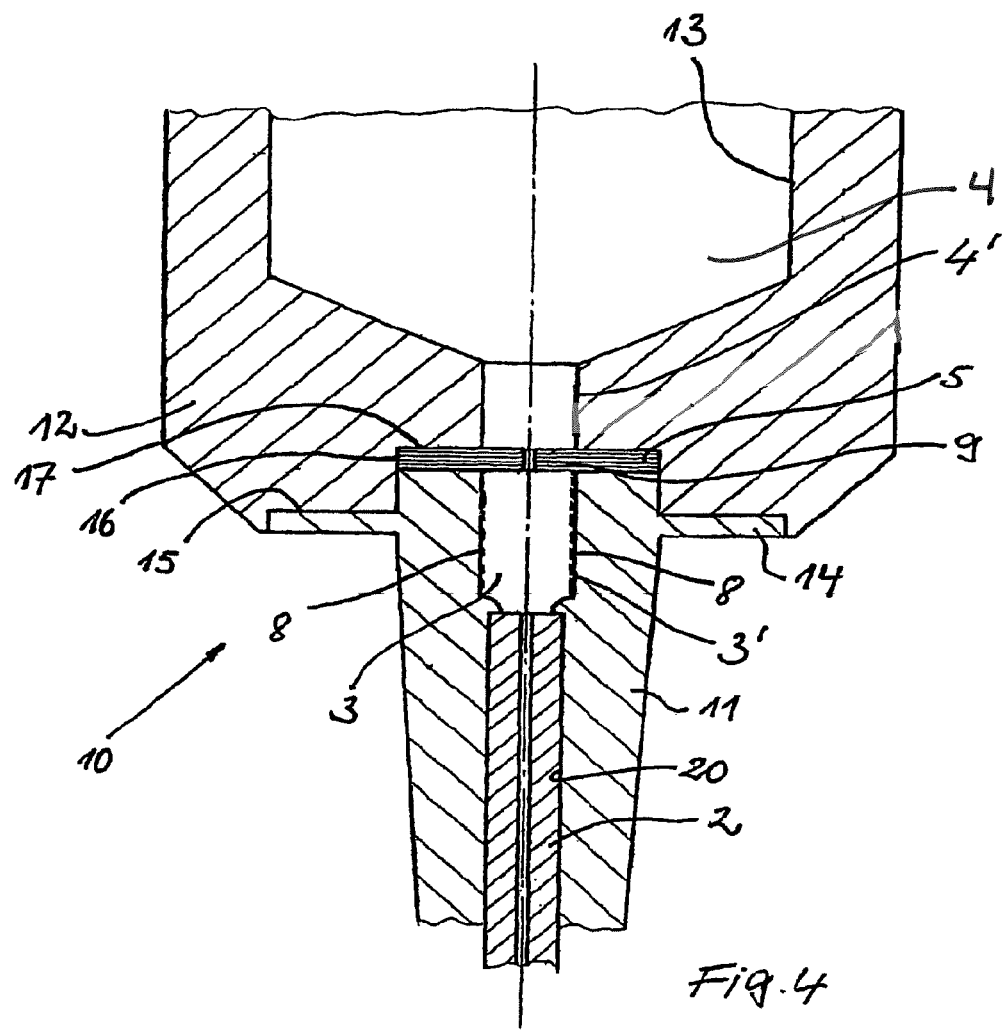
FIGS. 4 and 5 show further embodiments of the invention.

Described in detail below is the developed device 10 for the measurement of coagulation and/or aggregation of the blood, as a single use piece related to FIG. 4. Details of FIG. 4, which have already been described in connection with FIGS. 1 to 3, are indicated accordingly.

Basically the device 10 consists of a first casing 11 and a second casing 12, whereas the first casing 11 contains the capillary tube 2 and the prediffusing chamber 3. For example the capillary tube 2 can be closely inserted in the borehole 20 of the casing 11, whereas as seen in the direction of the blood stream, it is formed in the casing 11 behind the end of the capillary tube 2 of the prediffusing chamber 3 in such a way that it reaches the end of the casing 11. The inner surface of the side wall 3' of the pre-diffusing chamber 3 is provided with a coating 8.

The casing 12 contains a recess 16, which is closely connected to the after-diffusing chamber 4, which again flows into a blood collecting container 13 within the casing 12.

The porous piece 5 which contains the opening 9 is closely inserted in the recess 16 and is also inserted and closely attached to the end of the casing 11 which faces the porous piece 5. That way, the cases 11 and 12 form one unit, whereas the porous piece 5 lies closely between the surface of recess 16 which faces the piece and the end of case 11 and connects it with the after-diffusing chamber 4 of the case 12, so that no blood streams past the opening 9. Although this is not illustrated, the inner surface of the side wall 4' of the after-diffusing chamber 4 can optionally show a coating 8, whereas it is obvious, as has been described above, that either the prediffusing chamber 3 or the after-diffusing chamber 4 are provided with a coating 8.

The after-diffusing chamber 4, in particular, can be shaped according to FIGS. 2 and 3 and coated with the substance. In this case, the prediffusing chamber 3 can be omitted and the capillary tube 2 can go through the borehole 20 of the casing 11 before it reaches the opening 9.

Figure 5:
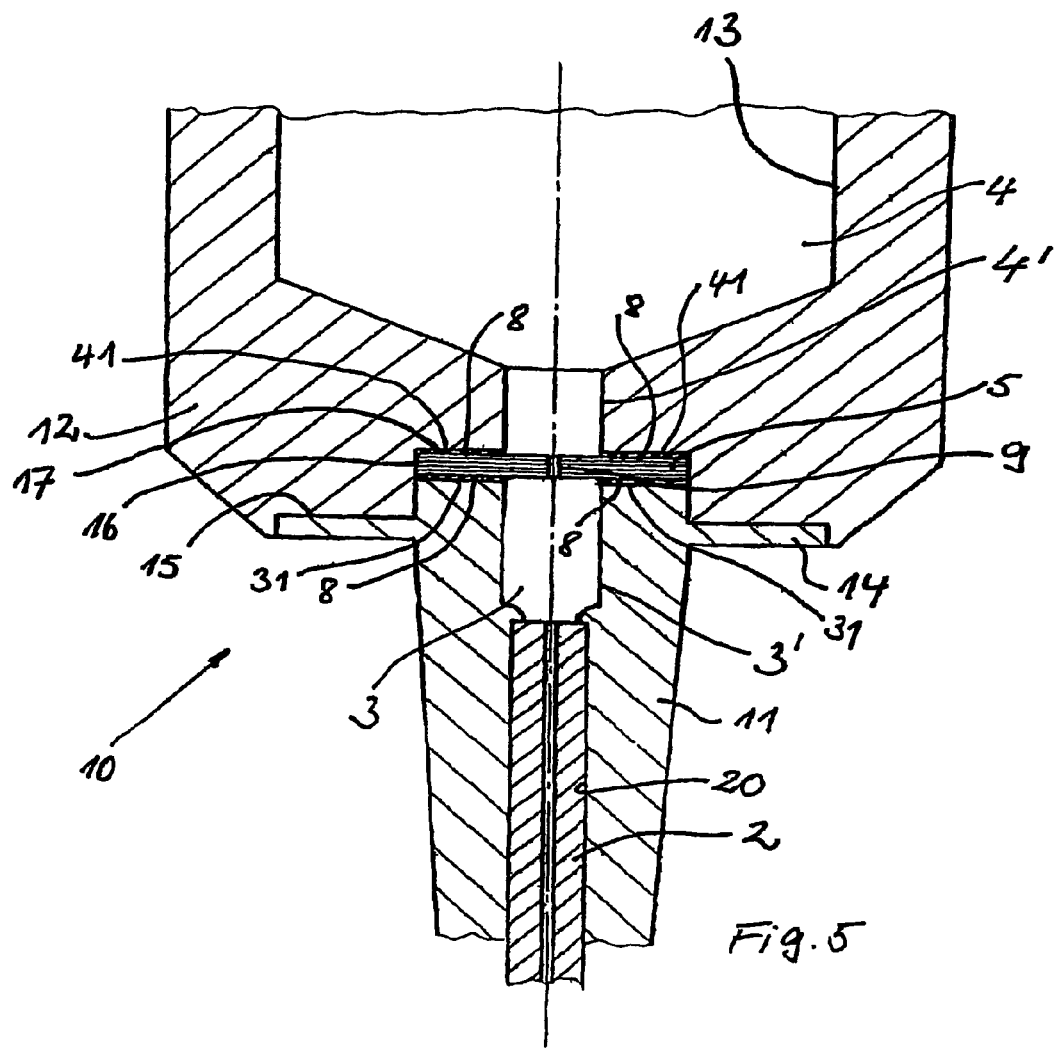

FIG. 5 shows an additional embodiment of the present invention, where the feeding of the substances occurs in the prediffusing chamber 3 and/or the after-diffusing chamber 4, respectively, from another chamber, which lies outside the prediffusing chamber 3 or the after-diffusing chamber 4, between the corresponding side of the porous piece 5 and the surfaces of the casing 11 or 12 containing the prediffusing chamber 3 or after-diffusing chamber 4. In doing so, the surface 31 surrounds the prediffusing chamber 3, whereas the porous piece 5 lies on the surface 31. Accordingly the surface 41 surrounds the after-diffusing chamber 4, whereas the surface 41 lies against the corresponding side of the porous piece 5. The surfaces 31 and/or 41 are coated with substance 8. The substances 8 proceed from the chamber between the surface 31 or 41, respectively, and the corresponding side of the porous piece 5 in the blood situated in the prediffusing chamber 3 or after-diffusing chamber 4, respectively, and to the opening 9. The specified chambers can thus be regarded as pieces of the pre- and after-diffusing chamber 3 and 4, respectively.

There has thus been shown and described a novel device for analyzing the coagulation or aggregation behavior of blood which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. In a device for the analysis of coagulation and/or aggregation reaction of blood, wherein the blood streams through an opening which located in a piece of porous material and wherein a substance which influences the blood aggregation can be applied to the blood, the improvement comprising an after-diffusing chamber disposed downstream of the opening to where blood streams from the opening, wherein the substance is applied to the blood from a coating on the walls of said after-diffusing chamber, and wherein the coating is applied to a surface of the walls of said after-diffusing chamber and not to the porous piece, said after-diffusing chamber being configured to redirect blood in a secondary stream back toward the opening via the porous piece.

2. Device according to claim 1, wherein said after-diffusing chamber has the coating on its side all adjacent the opening.

3. Device according to claim 2, wherein the side wall narrows towards the opening.

4. Device according to claim 3, wherein the side wall narrows in form of a cone.

5. Device according to claim 1, wherein the coating is applied on the entire surface of the wall of said after-diffusing chamber.

6. Device according to claim 1, wherein the coating is applied partially on the wall of said after-diffusing chamber.

7. Device according to claim 2, wherein the coating is further applied in a ring-shaped line which concentrically surrounds the longitudinal axis of the opening without contacting the porous piece, wherein said at least one line is continuous.

8. Device according to claim 2, wherein the coating is further applied in a ring-shaped line which concentrically surrounds the longitudinal axis of the opening without contacting the porous piece, wherein said at least one line is interrupted.

9. Device according to claim 8, wherein the at least one line of the coating is formed at a successive series of points.

10. Device according to claim 1, wherein the coating is applied in liquid form and subsequently dried.

11. Device according to claim 1, wherein the porous piece is provided with a collagen coating with dried collagen, at least in the area surrounding the opening on the side in the upstream direction.

12. Device according to claim 1, wherein the substance is selected from the group consisting of ADP, ristocetine, arachidonic acid, thrombine, epinephrine, thrombocyte activation factor (PAP) and thrombine-receptor-agonist-peptide (TBAP).

13. Process for the analysis of the coagulation and/or aggregation reaction of blood, in a device according to claim 1, wherein the substance which forms the coating is applied in liquid form on the walls of the at least one pre-diffusing chamber after-diffusing chamber and dries afterwards, and wherein the substance is reconstituted before performing a measurements with the device.

14. Process according to claim 13, wherein the reconstitution occurs through at least one of the addition of a liquid and the blood itself.

15. Process according to claim 14, wherein the fed liquid is a saline solution.

16. Process according to claim 13, wherein the applied substance is elected from the group consisting of ADP, ristocetine, arachidonic acid, thrombin, epinephrine, thrombocyte activation factor (PAF) and thrombin-receptor-agonist-peptide (TBAP).

17. Process according claim 13, wherein the coating is applied on the entire surface of the walls of the at least one pre-diffusing chamber and after-diffusing chamber.

18. Process according to claim 13, wherein the coating is applied partially on the walls of the at least one pre-diffusing chamber and after-diffusing chamber.

19. Process according to claim 13, wherein the coating is applied in at least one of a ring-shaped line and a surface which surrounds concentrically the longitudinal axis of the opening, on the walls of the at least one pre-diffusing chamber and after-diffusing chamber.

20. Process according to claim 19, wherein the coating is applied in the form of a continuous line or surface.

21. Process according to claim 19, wherein the coating is applied in form of an interrupted line or surface.

22. Process according to claim 21, wherein the line or surface is formed through application of a successive series of points of the substance.

23. Device according to claim 1, wherein the substance comprises at least one agent to be added to blood, thereby to enhance or inhibit the aggregation of blood cells.

24. Device according to claim 1, wherein the coating applied to the surface is continuous.

25. Device according to claim 1, wherein the coating applied to the surface is interrupted.

26. Device according to claim 25, wherein the coating is formed at a successive series of points.

27. Device according to claim 1, further comprising a pre-diffusing chamber upstream of the opening, from which blood can stream towards the opening, wherein the substance is also applied to the blood from a coating on the walls of said pre-diffusing chamber.

* * * * *